(12) United States Patent
Liu et al.

(10) Patent No.: US 8,690,426 B2
(45) Date of Patent: Apr. 8, 2014

(54) POSITION SENSING DEVICE FOR A PORTABLE DETECTION DEVICE

(75) Inventors: James Zhengshe Liu, Glenview, IL (US); Rowland Saunders, Hartland, WI (US); Kenneth Kump, Waukesha, WI (US); Donald Langler, Brookfield, WI (US); Roy Schley, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 211 days.

(21) Appl. No.: 12/815,148

(22) Filed: Jun. 14, 2010

(65) Prior Publication Data

US 2011/0305319 A1    Dec. 15, 2011

(51) Int. Cl.
*A61B 6/08*        (2006.01)
*H05G 1/64*        (2006.01)

(52) U.S. Cl.
USPC ...... 378/205; 378/98.8; 378/189; 250/370.09

(58) Field of Classification Search
USPC ........ 378/98.8, 162, 165, 189, 191, 196, 197, 378/198, 205; 250/370.09
See application file for complete search history.

(56) References Cited

U.S. PATENT DOCUMENTS

| | | | | |
|---|---|---|---|---|
| 5,649,237 A | * | 7/1997 | Okazaki | 396/55 |
| 5,953,683 A | * | 9/1999 | Hansen et al. | 702/95 |
| 6,092,928 A | * | 7/2000 | Mattson et al. | 378/205 |
| 6,539,639 B2 | * | 4/2003 | Smith | 33/356 |
| 6,725,173 B2 | * | 4/2004 | An et al. | 702/141 |
| 6,810,738 B2 | * | 11/2004 | Sakaguchi | 73/510 |
| 6,890,099 B2 | * | 5/2005 | Tanaka et al. | 378/205 |
| 7,046,764 B1 | * | 5/2006 | Kump | 378/117 |
| 7,065,393 B2 | | 6/2006 | Sati et al. | |
| 7,127,032 B1 | | 10/2006 | Kump | |
| 7,305,315 B2 | * | 12/2007 | Kwon et al. | 702/92 |
| 7,533,569 B2 | * | 5/2009 | Sheynblat | 73/510 |
| 7,545,914 B2 | * | 6/2009 | Kito et al. | 378/98.8 |
| 7,573,034 B2 | * | 8/2009 | Heath et al. | 250/361 R |
| 7,581,885 B2 | | 9/2009 | Ertel et al. | |
| 7,590,221 B2 | * | 9/2009 | Durack | 378/165 |
| 7,622,889 B2 | * | 11/2009 | Spahn | 320/101 |
| 7,643,615 B2 | * | 1/2010 | Wang et al. | 378/165 |
| 7,664,222 B2 | * | 2/2010 | Jabri et al. | 378/26 |
| 7,744,279 B2 | * | 6/2010 | Heath et al. | 378/205 |
| 7,775,713 B2 | * | 8/2010 | Klemola et al. | 378/191 |
| 7,806,591 B2 | * | 10/2010 | Wang et al. | 378/206 |
| 7,869,568 B2 | * | 1/2011 | Yokoyama et al. | 378/98.8 |
| 8,019,045 B2 | * | 9/2011 | Kato | 378/116 |

* cited by examiner

*Primary Examiner* — Allen C. Ho
(74) *Attorney, Agent, or Firm* — The Small Patent Law Group; Dean D. Small (57) ABSTRACT

A method of fabricating a portable x-ray detector includes coupling a gravity sensor to the portable x-ray detector and coupling a processor to the gravity sensor. The processor is programmed to receive an input from the gravity sensor, determine a physical orientation of the portable x-ray detector based on the received input, and generate an indication to reposition the portable x-ray detector. A portable detector and an imaging system including the portable detector are also provided.

18 Claims, 5 Drawing Sheets

POSITION SENSING DEVICE FOR A PORTABLE DETECTION DEVICE

BACKGROUND OF THE INVENTION

The subject matter disclosed herein relates generally to imaging detectors, and more particularly to a sensor for positioning a portable imaging detector.

In various medical imaging applications, a portable imaging detector may be utilized to perform medical imaging. At least one conventional portable x-ray detector includes a housing and various components installed within the housing to enable the imaging detector to be utilized in x-ray imaging applications.

During imaging procedures, it is desirable to orient the portable x-ray detector with respect to the x-ray source to improve image quality. Portable x-ray detectors are typically manually aligned, by the operator, with the x-ray source. However, in some cases the operator may position the x-ray detector out of alignment with respect to the x-ray source. For example, an operator may improperly position the portable x-ray detector such that the detection surface, e.g. the front face of the portable x-ray detector is either improperly aligned with the x-ray source or facing away from the x-ray source.

BRIEF DESCRIPTION OF THE INVENTION

In one embodiment, a method of fabricating a portable x-ray detector is provided. The method includes coupling a gravity sensor to the portable x-ray detector and coupling a processor to the gravity sensor. The processor is programmed to receive an input from the gravity sensor, determine a physical orientation of the portable x-ray detector based on the received input, and generate an indication to reposition the portable x-ray detector.

In another embodiment, a portable x-ray detector is provided. The portable detector includes a detector panel including a plurality of detector elements, a gravity sensor installed within a portable detector, and a processor coupled to the gravity sensor. The processor is programmed to receive an input from the gravity sensor, determine a physical orientation of the portable x-ray detector based on the received input, and generate an indication to reposition the portable x-ray detector based on the determined physical orientation.

In a further embodiment, a medical imaging system is provided. The imaging system includes an x-ray source and a portable x-ray detector configured to receive x-rays generated by the x-ray source. The portable x-ray detector includes a gravity sensor installed within a portable detector, and a processor coupled to the gravity sensor. The processor is programmed to receive an input from the gravity sensor, generate orientation information that represents a physical orientation of the portable x-ray detector based on the received input from the gravity sensor, and transmit the orientation information to a workstation to enable an operator to reposition the portable x-ray detector based on the determined physical orientation.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Figure 1:
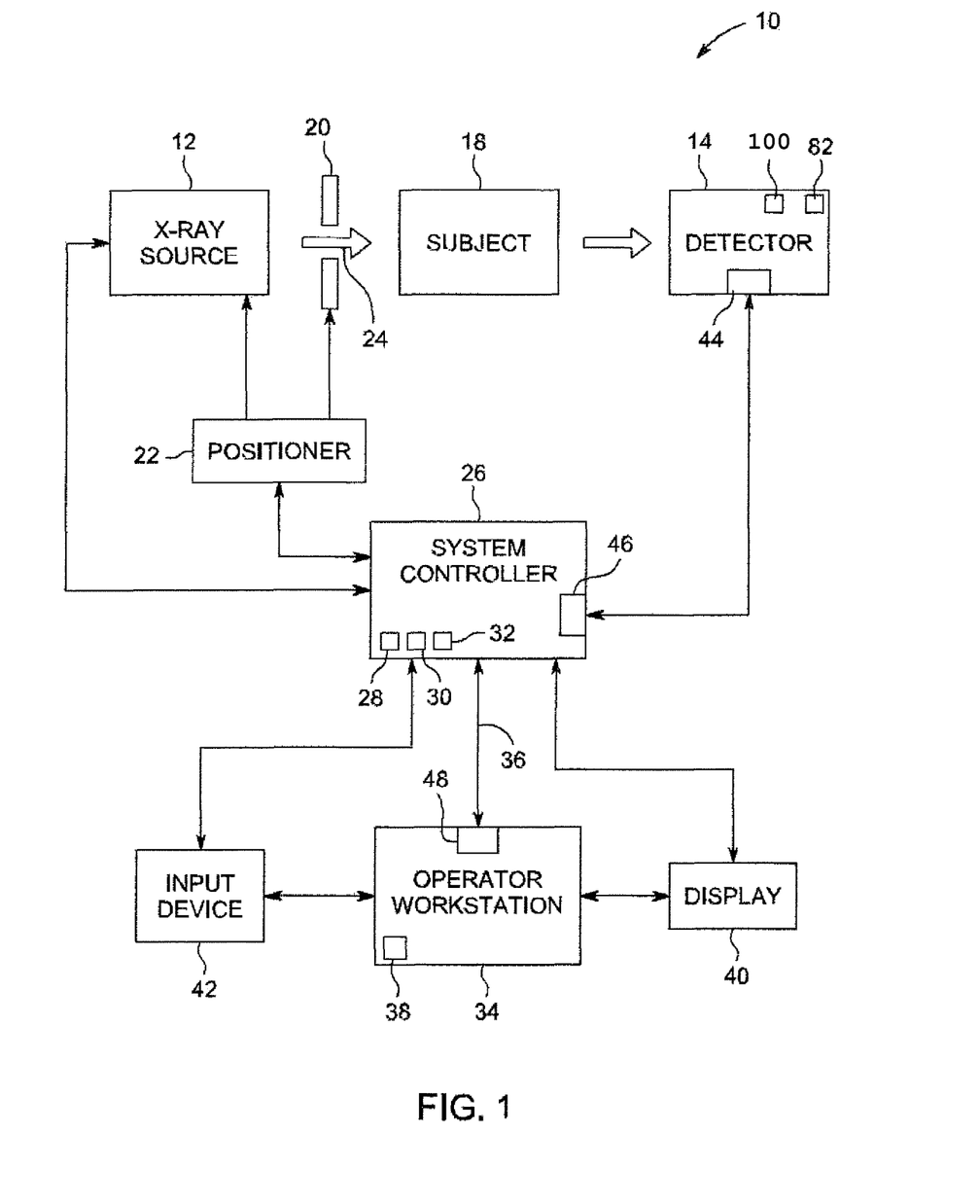
FIG. 1 is a block schematic diagram of the exemplary medical imaging system in accordance with various embodiments.

Referring to the drawings, FIG. 1 is a block schematic diagram of an exemplary imaging system 10 formed in accordance with an embodiment of the present invention. The various embodiments described herein are not limited to a medical imaging system for imaging human subjects, but may include veterinary or non-medical systems for imaging non-human objects, or non-destructive testing systems (e.g. airport baggage systems) etc.

The medical imaging system 10 in the preferred embodiment is a digital radiography imaging system 10 that includes an x-ray source 12 and a detector 14. The x-ray source 12 may be mounted to a gantry (not shown). Optionally, the x-ray source 12 may be movable by an operator. The imaging system 10 may also include a collimator 20 that is disposed between the x-ray source 12 and the subject 18. The imaging system 10 may also include a positioner 22. The positioner 22 is a mechanical controller coupled to the x-ray source 12 and collimator 20 for controlling the positioning of the x-ray source 12 and the collimator 20.

During operation, the imaging system 10 generates images of the subject 18 by means of an x-ray beam 24 emitted by the x-ray source 12, and passing through the collimator 20. The collimator 20 forms and confines the x-ray beam 24 to a desired region, wherein the subject 18, such as a human patient, an animal or an object, is positioned. A portion of the x-ray beam 24 passes through or around the subject 18 and, being altered by attenuation and/or absorption by tissues within the subject 18, continues on toward and impacts the detector 14. In the exemplary embodiment, the detector 14 is a portable digital flat panel x-ray detector that is not physically coupled to the x-ray source 12. During operation, the detector 14 converts x-ray photons received by the detector 14 to lower energy light photons, and subsequently to electric signals, which are acquired and processed to reconstruct an image of internal anatomy of the subject 18.

The imaging system 10 further includes a system controller 26 coupled to the x-ray source 12, the detector 14, and the positioner 22 for controlling operation of the x-ray source 12, the detector 14, and the positioner 22. The system controller 26 may supply both power and control signals for imaging examination sequences. In general, the system controller 26 controls the operation of the imaging system 10 to execute examination protocols and to process acquired image data. The system controller 26 may also include signal processing circuitry, based on a general purpose or application-specific computer, associated memory circuitry for storing programs and routines executed by the computer, as well as configuration parameters and image data, interface circuits, and so forth.

The system controller 26 may further include at least one computer or processor 28 that is configured to coordinate the operation of the x-ray source 12, the detector 14, and the positioner 22, and to process image data acquired from the detector 14. As used herein, the term "computer" may include any processor or processor-based system including systems using controllers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer". During operation, the processor 28 carries out various functionality in accordance with routines stored in an associated memory circuitry 30. The associated memory circuitry 30 may also serve to store configuration parameters, imaging protocols, operational logs, raw and/or processed image data, and so forth.

The system controller 26 may further include interface circuitry 32 that permits an operator or user to define imaging protocols, imaging sequences, determine the operational status and health of system components, and so-forth. The interface circuitry 32 may allow external devices to receive images and image data, and command operation of the radiography system, configure parameters of the system, and so forth.

The system controller 26 may be coupled to a range of external devices via a communications interface. Such devices may include, for example, an operator workstation 34 for interacting with the system controller 26 or directly to the detector 14, processing or reprocessing images, viewing images, and so forth. The operator workstation 34 may be embodied as a personal computer (PC) that is positioned near the imaging system 10 and hardwired to the system controller 26 via a communication link 36. The workstation 34 may also be embodied as a portable computer such as a laptop computer or a hand-held computer that transmits information to the system controller 26. In one embodiment, the communication link 36 may be hardwired between the system controller 26 and the workstation 34. Optionally, the communication link 36 may be a wireless communication link that enables information to be transmitted to or from the workstation 34 to the system controller 26 wirelessly. In the exemplary embodiment, the workstation 34 controls real-time operation of the imaging system 10. The workstation 34 is also programmed to perform medical image diagnostic acquisition and reconstruction processes described herein.

The operator workstation 34 includes a central processing unit (CPU) or computer 38, a display 40 and an input device 42. In the exemplary embodiment, the computer 38 executes a set of instructions that are stored in one or more storage elements or memories, in order to process input data. The storage elements may also store data or other information as desired or needed. The storage elements may be in the form of an information source or a physical memory element within the computer 38. The set of instructions may include various commands that instruct the computer or processor 38 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The CPU 38 connects to the communication link 36 and receives inputs, e.g., user commands, from the input device 42. The input device 42 may be, for example, a keyboard, mouse, a touch-screen panel, and/or a voice recognition system, etc. Through input device 42 and associated control panel, switches, the operator may control the operation of the imaging system 10 and the positioning of the x-ray source 12 for a scan. Similarly, the operator may control the display of the resulting image on the display 40 and can perform image-enhancement functions using programs executed by the workstation CPU 38. The workstation 34 may also be linked to the system controller 26 by any one or more network links.

In the exemplary embodiment, to transmit the electric signals from the detector 14 to the system controller 26 or the workstation 34, the detector 14 includes a transceiver 44 that is configured to transmit the electrical signals and other information generated by the detector 14 in a wireless format to a corresponding transceiver 46 that is mounted in the system controller 26. Optionally, the transceiver 44 is configured to transmit the electrical signals and other information generated by the detector 14 in a wireless format to a corresponding transceiver 48 that is mounted in the workstation 34.

Figure 2:
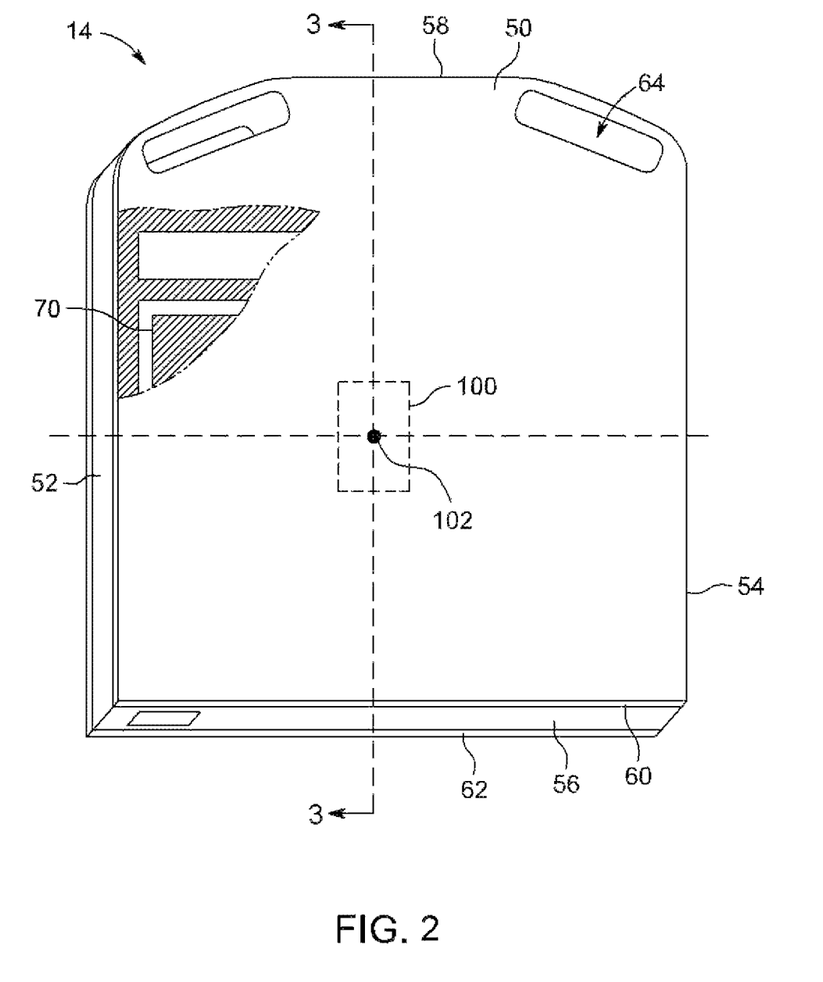
FIG. 2 is a top cut-away view of the exemplary x-ray detector shown in FIG. 1 in accordance with various embodiments.

FIG. 2 is a bottom cut-away view of the exemplary portable detector 14 shown in FIG. 1. In the exemplary embodiment, the portable detector 14 is hand-carried by an operator to various locations to perform medical imaging. Additionally the portable detector 14 may be mounted on a wheeled cart or other movable apparatus to enable an operator to move the detector 14 from one location to another location.

As shown in FIG. 2, the portable detector 14 includes a casing 50. The casing 50 is formed to include a pair of sidewalls 52 and 54, a bottom side 56, and an opposing top side 58. The casing 50 also includes a front cover 60, shown as a surface parallel to the plane of the illustration, and an opposing back cover 62. The casing 50 also includes at least one slot 64 that extends from the front cover 60 to the back cover 62. During operation, the slot 64 functions as a handle to enable an operator to transport the portable detector 14. Specifically, the slot 64 can be used to mount and/or carry the portable detector 14. The sidewalls, top and bottom walls, the front and back covers together form the casing 50. The casing 50 may be fabricated, for example, from a lightweight, low atomic number (N) material, such as aluminum, or a graphite material. Graphite has a lower weight than aluminum, but it is also stiffer and less energy-absorbent.

In the exemplary embodiment, the detector 14 also includes a sensor 100 that is installed internally within the casing 50. In the exemplary embodiment, the sensor 100 is a gravity sensor that is utilized to determine a physical orientation of the portable x-ray detector 14. More specifically, the sensor 100 is configured to generate positional information that represents the physical orientation of the detector 14 with respect to the earth or ground. The information generated by the sensor 100 is utilized by the operator to reposition the portable detector 14 such that the portable detector 14 is aligned with the x-ray source 12. Moreover, the information generated by the sensor 100 may also be utilized to reorient images generated by the imaging system 10. As shown in FIG. 2, in one embodiment, the sensor 100 is located approximately near a center point 102 of the detector 14. For example, as shown in FIG. 2, an x-axis extends vertically through the center point 102 or focal point of the detector 14. Moreover, the y-axis extends horizontally through the center point 102 or focal point of the detector 14 and is approximately perpendicular to the x-axis. Accordingly, the x-axis and the y-axis intersect at the center point 102 of the detector 14 and the sensor 100 is installed proximate to the center point 102. The sensor 100 is discussed in more detail below.

Figure 3:
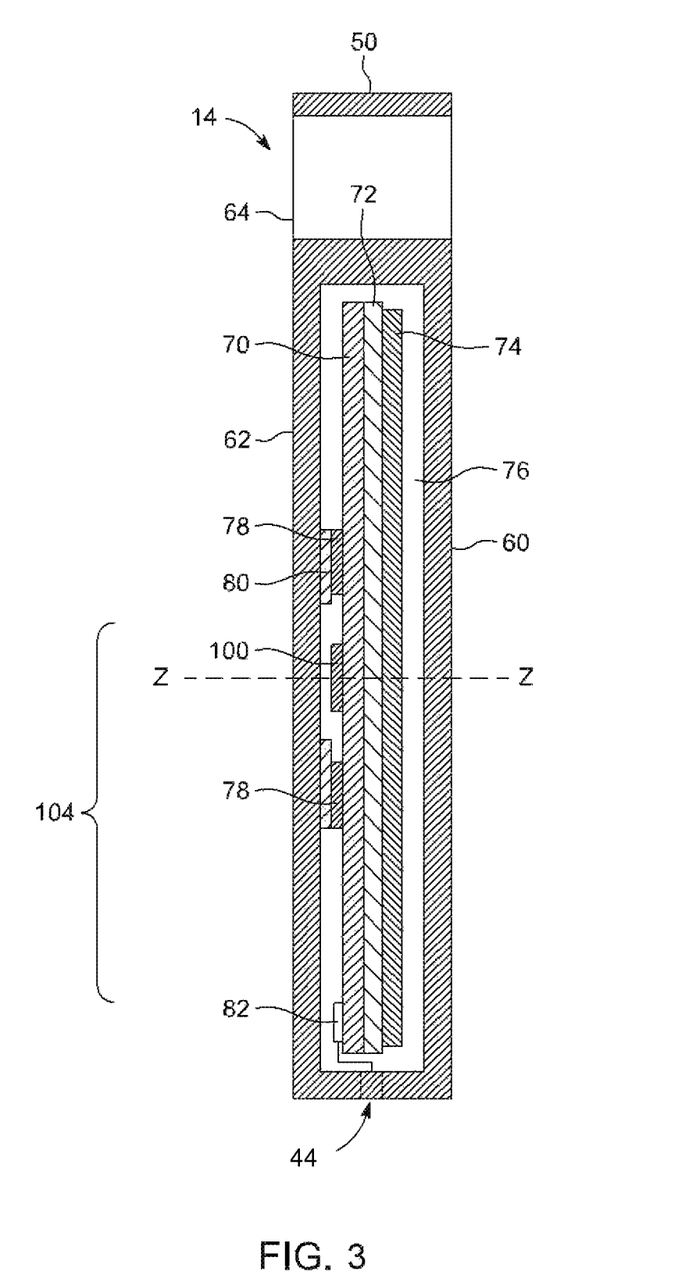
FIG. 3 is a side cut-away view of the detector shown in FIG. 2 in accordance with various embodiments.

FIG. 3 is a side cut-away view of the portable detector 14 shown in FIG. 2 viewed along the line 3-3 of FIG. 2. As shown in FIG. 3, the detector 14 also includes a circuit board 70 that is affixed (e.g., using an adhesive) to a panel support 72 that may be fabricated from a low N material, which in turn is affixed to a panel 74. The panel 74 may be a glass panel and may include x-ray scintillator material. During operation, the panel 74 is formed to include a plurality of detector rows that each include a plurality of detector elements (not shown), that together sense the projected x-rays that pass through an object, such as a patient. During operation, each detector element produces an electrical signal that represents the intensity of an imaging X-ray beam and hence allows estimation of the attenuation of the beam as the beam passes through the subject 18. In some embodiments, the panel support 72 is not used, and circuit board 70 is affixed directly to the panel 74. Together, circuit board 70 and panel 74 (and panel support 72, if present) comprise an "electronic assembly."

To provide some degree of break resistance for panel 74, a gap 76 is provided between the panel 74 and the front cover 60. Also, the electronic assembly is clear of any wall of the casing, but is mounted to the back cover 62. Additionally, heat generating components 78 on the circuit board 70 may be thermally coupled to back cover 62 using a heat conducting compound 80. The heat conducting compound 80 provides, directly or indirectly, a mechanical coupling between the circuit board 70 and the back cover 62. The portable detector 14 also includes a processor 82 and the sensor 100 that are each mounted to the circuit board 70. The processor 82 is configured to receive orientation information from the sensor 100 and transmit the orientation information to a remote location, such as for example, the workstation 34. The processor 82 is also configured to store the orientation information and other information that is utilized to operate the portable detector 14 and/or to transmit information to a remote location via the wireless transceiver 44 as discussed above. In the exemplary embodiment, the detector 14 is portable, but typically large enough to image a significant region of a human patient, such as a patient's chest. Thus, the portable detector 14 may be only about one or a few centimeters in thickness, but may be tens of centimeters in width and length.

Figure 4:
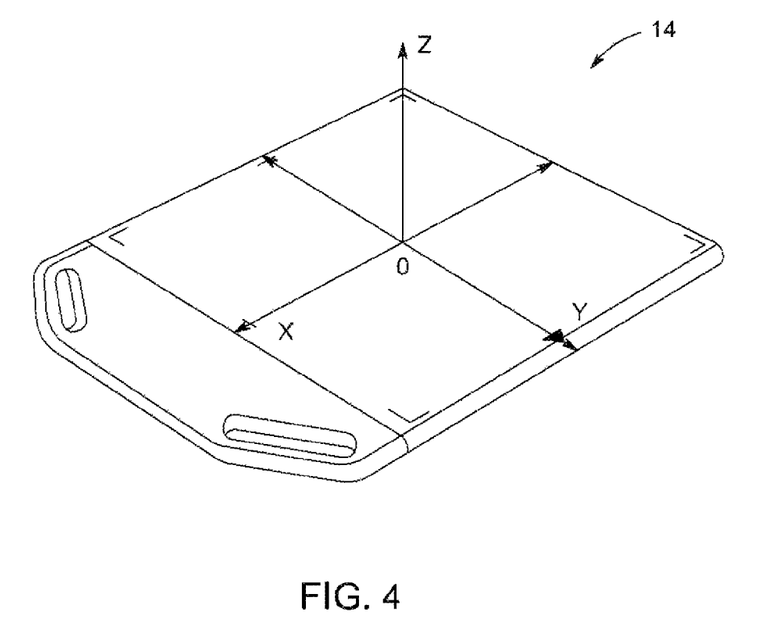
FIG. 4 is a top perspective view of the portable detector shown in FIGS. 1-3 in accordance various embodiments.

To explain the general operation of the portable detector 14, including the sensor 100, reference is now made to FIG. 4. FIG. 4 is a top perspective view of the portable detector 14 shown in FIGS. 1-3. In the exemplary embodiment, the processor 82 and the sensor 100 form a detector orientation circuit 104 that is utilized to process information generated by the sensor 100 and transmit the information to a remote location such as workstation 34. In the exemplary embodiment, the sensor 100 is a 3-axis gravity sensor that is configured to detect changes in the center of gravity of the detector 14. More specifically, the output from the sensor 100, for each of the 3-axes is dependent on the angle formed between each respective axis and the earth's gravity.

For example, as shown in FIG. 4, the x-axis and the y-axis of the portable detector 14 are both approximately parallel to the plane of the detector 14. More specifically, the x-axis and the y-axis are both approximately parallel to the image surface of the detector 14. Moreover, the z-axis is approximately perpendicular or normal to both the x-axis and the y-axis. Therefore, the output from the gravity sensor 100 for the first or x-axis represents the angle between the x-axis and the earth's gravity. The output from the gravity sensor 100 for the second or y-axis represents the angle between the y-axis and the earth's gravity. Moreover, the output from the gravity sensor 100 for the third or z-axis represents the angle between the z-axis and the earth's gravity.

Figure 5:
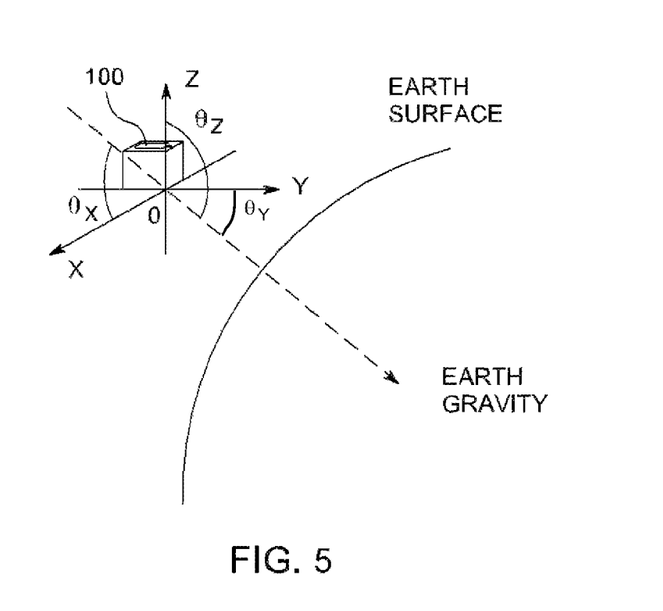
FIG. 5 is a graphical illustration of an exemplary method of operating the detector shown in FIGS. 1-3 in accordance various embodiments. I.

FIG. 5 is a graphical illustration that is utilized to explain a method of determining the orientation of the detector 14 using the gravity sensor 100 described above. During operation, the 3-axis gravity sensor 100 determines an angle $\theta_x$ that is formed between the x-axis or the portable detector 14 and the earth's gravitational field. The 3-axis gravity sensor 100 determines an angle $\theta_y$ that is formed between the y-axis of the portable detector 14 and the earth's gravitational field and an angle $\theta_z$ that is formed between the z-axis of the portable detector 14 and the earth's gravitational field.

The imaging system 10 utilizes the angles determined by the gravity sensor 100, $\theta_x$, $\theta_y$, and $\theta_z$ to generate three corresponding vectors $a_x$, $a_y$, and $a_z$. In the exemplary embodiment, the three vectors $a_x$, $a_y$, and $a_z$ are calculated in accordance with:

$$\begin{cases} a_x = g \times \cos(\theta_x) \\ a_y = g \times \cos(\theta_y) \\ a_z = g \times \cos(\theta_z) \end{cases} \quad (1)$$

wherein g represents the earth's gravitational pull.

The imaging system 10 then calculates the exact orientation of the detector 14 in accordance with:

$$\begin{cases} \theta_x = \cos^{-1}\left(\frac{a_x}{g}\right) \\ \theta_y = \cos^{-1}\left(\frac{a_y}{g}\right) \\ \theta_z = \cos^{-1}\left(\frac{a_z}{g}\right) \end{cases} \quad (2)$$

During operation, when the detector 14 is positioned parallel to the earth or ground, the gravities (g) in both the x and y directions are zero. If the detector 14 is repositioned such that the detector 14 is not parallel to the earth or ground, the values of at least one of $\theta_x$ or $\theta_y$ as determined by the gravity sensor 100 also change. For example, assuming that the detector 14 is tilted along the x-axis. Based on the tilt of the detector 14 along the x-axis, the gravity sensor 100 may determine that the gravity in the x-direction is −1.0 g. Moreover, if the imaging surface of the detector 14 is positioned to face the x-ray source 12, the gravity in z direction may be approximately −1.0 g. However, if the detector 14 is positioned to face away from the x-ray source 12, the gravity in z direction may be approximately +1.0 g.

The information acquired by the gravity sensor 100 is transmitted from the gravity sensor 100 to a remote location, such as the workstation 34. In the exemplary embodiment, the workstation 34 is configured to analyze the information generated by the gravity sensor 100 and generate at least one of an audio or visual indication that represents the current alignment or orientation of the detector 14.

In one embodiment, the workstation 34 may generate a visual indication on the display 40. The visual or audible indication represents the current orientation of the detector 14. The operator may then adjust the detector 14 based on the information displayed on the display 14. Optionally, the workstation 34 may generate commands that instruct an operator on repositioning the detector 14 such that the detector 14 is aligned with the x-ray source 12. For example, the workstation 34 may generate a command that instructs the operator to rotate the detector 14 in one of the x, y, or z directions such that the orientation of the detector 14 is aligned with the x-ray source 12.

In another embodiment, the workstation 34 may inhibit the operation of the x-ray source 12 based on the information received from the gravity sensor 100. For example, when the detector 14 is placed with the detection surface facing away from the x-ray source 12, the workstation 34 may inhibit the operator from operating the x-ray source 12. The workstation 34 may also generate a visual or audible indication to enable the operator to reorient the detector 14 with respect to the x-ray source 12. After, the detector 14 is aligned with the x-ray source 12, based on information received from the gravity sensor 100, the workstation may then enable the operator to activate the x-ray source 12 to perform any desired imaging operations.

Figure 6A:
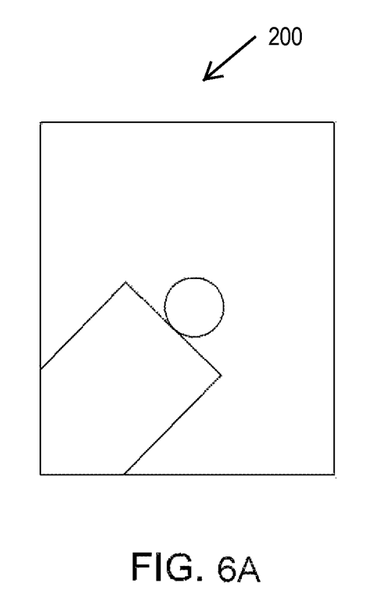
FIG. 6A is an exemplary image generated in accordance with various embodiments.
Figure 6B:
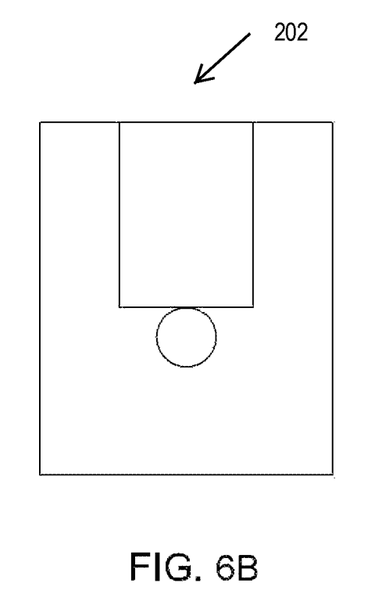
FIG. 6B is an exemplary image generated in accordance with various embodiments.
Figure 6C:
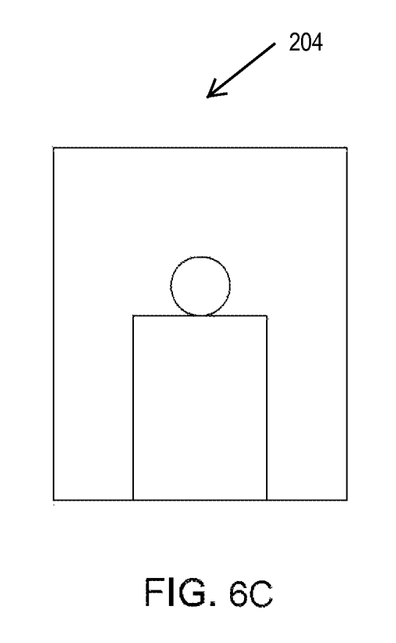
FIG. 6C is an exemplary image generated in accordance with various embodiments.

In another embodiment, the information generated by the gravity sensor 100 may be utilized to rotate or otherwise re-orient an image displayed on the display 40 (shown in FIG. 1). For example, FIG. 6A represents an exemplary image 200 generated by the detector 14 when the detector 14 is improperly aligned along the x-axis and/or the y-axis based on information received from the gravity sensor 100. FIG. 6B represents an exemplary image 202 generated by the detector 14 when the detector 14 is upside down with respect to the subject being imaged. In both embodiments, the detection surface of the detector 14 is substantially aligned with the x-ray source 12. However, the detector 14 is disposed at an angle such that images generated by the imaging system 10, e.g. images 200 and 202, are displayed on the display 40 at an angle or orientation that is not optimal for viewing by the operator. Accordingly, in this embodiment, the workstation 34 may utilize the information generated by the gravity sensor 100 to reorient either the image 200 or the image 200 to a "heads up" orientation shown in the image 204 in FIG. 6C. Accordingly, information generated by the gravity sensor 100 is utilized to rotate images generated by the imaging system 10 such that the displayed images are oriented in the "heads-up" orientation. Re-orientating displayed images in the "heads up" orientation is particularly useful when utilized in digital cassette applications such as cross table lateral and wheelchair examinations because the orientation of the detector 14 is not controlled by the imaging system 10.

Described herein is a portable detector 14 that includes a 3-axis gravity sensor that is installed within the portable detector. During operation, the 3-axis gravity sensor generates orientation information that is utilized to determine the orientation of the portable detector with respect to the earth ground. The information generated by the gravity sensor is transmitted to an imaging system. The information may be transmitted via a wired or wireless connection to the imaging system. The information generated by the gravity sensor may be utilized to inform an operator that the portable detector is improperly positioned with respect to an x-ray source. Moreover, the information may be utilized to inhibit the x-ray source from generating x-rays based on the orientation of the portable detector. The information may also be utilized by the imaging system to reorient or rotate an image that is generated by the imaging system to an orientation that improves the user's ability to read or interpret the image. For example, the image may be rotated such that a patient's head is located at the top of the display device rather than a side or bottom of the display device.

A technical effect of the various embodiments is to provide a portable detector that is capable of notifying an operator when the portable detector is improperly oriented with respect to either the x-ray source, the earth, or the patient being imaged. A visual or audible indication enables the operator to reorient either the portable detector or the image generated by the portable detector.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose various embodiments of the invention, including the best mode, and also to enable any person skilled in the art to practice the various embodiments, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method comprising:
   coupling a 3-axis gravity sensor to a portable x-ray detector;
   coupling a processor to the 3-axis gravity sensor and to a workstation, the processor being programmed to perform a processing method comprising:
      transmitting orientation information corresponding to a physical orientation of the portable x-ray detector determined using the 3-axis gravity sensor to the workstation; and
   generating, with the workstation, a command that instructs an operator to rotate the portable x-ray detector in at least one direction to align the portable x-ray detector with an x-ray source based on the physical orientation of the portable x-ray detector determined using the 3-axis gravity sensor.

2. A method in accordance with claim 1, wherein coupling the 3-axis gravity sensor to the portable x-ray detector comprises:
   coupling the 3-axis gravity sensor proximate to a centerpoint of the portable x-ray detector.

3. A method in accordance with claim 1 wherein the processing method which the processor is programmed to perform comprises:
   receiving a wireless request from a workstation; and
   wirelessly transmitting orientation information from the 3-axis gravity sensor to the workstation, the orientation information representing the physical orientation of the portable x-ray detector with respect to the earth.

4. A method in accordance with claim 1 further comprising re-orienting, with the workstation, a displayed image based on the orientation information.

5. A method in accordance with claim 1 further comprising generating, with the workstation, an indication representing an alignment of the portable x-ray detector with respect to an x-ray source.

6. A method in accordance with claim 1 further comprising inhibiting, with the workstation, an operation of an x-ray source based on the received orientation information.

7. A system comprising:
   a workstation; and
   a portable x-ray detector comprising:
      a detector panel including a plurality of detector elements;
      a 3-axis gravity sensor installed within the portable x-ray detector; and
      a processor, the processor programmed to:
         transmit orientation information corresponding to a physical orientation of the portable x-ray detector determined using the 3-axis gravity sensor to the workstation, wherein the workstation is configured to generate a command that instructs an operator to rotate the portable x-ray detector in at least one direction to align the portable x-ray detector with an x-ray source.

8. A system in accordance with claim 7 wherein the 3-axis gravity sensor is coupled proximate to a centerpoint of the portable x-ray detector.

9. A system in accordance with claim 7 wherein the processor is further programmed to:
   receive a wireless request from the workstation; and
   wirelessly transmit orientation information from the 3-axis gravity sensor to the workstation, the orientation information representing the physical orientation of the portable x-ray detector with respect to the earth.

10. A system in accordance with claim 7 wherein the workstation is configured to re-orient a displayed image based on the orientation information.

11. A system in accordance with claim 7 wherein the workstation is further configured to generate an indication representing an alignment of the portable x-ray detector with respect to an x-ray source.

12. A system in accordance with claim 7 wherein the workstation is further configured to inhibit an operation of an x-ray source based on the received orientation information.

13. A medical imaging system comprising:
    an x-ray source;
    a workstation; and
    a portable x-ray detector configured to receive x-rays generated by the x-ray source, the portable x-ray detector including a 3-axis gravity sensor installed within the portable x-ray detector, and a processor coupled to the 3-axis gravity sensor, the processor programmed to transmit orientation information corresponding to a physical orientation of the portable x-ray detector determined using the 3-axis gravity sensor to the workstation, wherein the workstation is configured to generate a command that instructs an operator to rotate the portable x-ray detector in at least one direction to align the portable x-ray detector with the x-ray source.

14. A medical imaging system in accordance with claim 13 wherein the 3-axis gravity sensor is coupled proximate to a centerpoint of the portable x-ray detector.

15. A medical imaging system in accordance with claim 13 wherein the processor is further programmed to wirelessly transmit the orientation information from the 3-axis gravity sensor to the workstation, the orientation information representing the physical orientation of the portable x-ray detector with respect to the earth.

16. A medical imaging system in accordance with claim 13 wherein the workstation is configured to generate an image of an object, and re-orient the image based on the orientation information.

17. A medical imaging system in accordance with claim 13 wherein the workstation is further configured to generate an indication representing an alignment of the portable x-ray detector with respect to the x-ray source.

18. A medical imaging system in accordance with claim 13 wherein the workstation is configured to inhibit the operation of the x-ray source based on the orientation information.

* * * * *